US012594320B2

(12) United States Patent
Salem et al.

(10) Patent No.: US 12,594,320 B2
(45) Date of Patent: Apr. 7, 2026

(54) METHOD FOR TREATING CHECKPOINT INHIBITORS INDUCED ADVERSE EVENTS

(71) Applicants: ASSISTANCE PUBLIQUE—HÔPITAUX DE PARIS, Paris (FR); SORBONNE UNIVERSITÉ, Paris (FR); INSTITUT NATIONAL DE LA SANTÉ ET DE LA RECHERCHE MÉDICALE (INSERM), Paris (FR); VANDERBILT UNIVERSITY, Nashville, TN (US)

(72) Inventors: Joe-Elie Salem, Paris (FR); Yves Allenbach, Paris (FR); Mathieu Kerneis, Paris (FR); Javid Moslehi, Nashville, TN (US); Douglas Johnson, Nashville, TN (US)

(73) Assignees: ASSISTANCE PUBLIQUE—HÔPITAUX DE PARIS, Paris (FR); SORBONNE UNIVERSITÉ, Paris (FR); INSTITUT NATIONAL DE LA SANTÉ ET DE LA RECHERCHE MÉDICALE (INSERM), Paris (FR); VANDERBILT UNIVERSITY, Nashville, TN (US)

( * ) Notice: Subject to any disclaimer, the term of this patent is extended or adjusted under 35 U.S.C. 154(b) by 1111 days.

(21) Appl. No.: 17/427,698

(22) PCT Filed: Feb. 3, 2020

(86) PCT No.: PCT/EP2020/052554
§ 371 (c)(1),
(2) Date: Aug. 2, 2021

(87) PCT Pub. No.: WO2020/161045
PCT Pub. Date: Aug. 13, 2020

(65) Prior Publication Data
US 2022/0125880 A1 Apr. 28, 2022

(30) Foreign Application Priority Data
Feb. 4, 2019 (EP) ..................................... 19305128

(51) Int. Cl.
A61K 38/17 (2006.01)
A61K 45/06 (2006.01)
A61P 37/02 (2006.01)

(52) U.S. Cl.
CPC .......... A61K 38/1774 (2013.01); A61K 45/06 (2013.01); A61P 37/02 (2018.01)

(58) Field of Classification Search
CPC .. A61K 38/1774; A61K 45/06; A61K 31/506; A61P 37/02
See application file for complete search history.

(56) References Cited

U.S. PATENT DOCUMENTS 10,052,360 B2    8/2018   Cohen et al.

FOREIGN PATENT DOCUMENTS

| WO | 2005016266 A2 | 2/2005 | |
|---|---|---|---|
| WO | 2014004857 A1 | 1/2014 | |
| WO | WO-2017165742 A1 * | 9/2017 | ......... C07K 16/2839 |
| WO | 2018053506 A1 | 3/2018 | |
| WO | 2020161045 A1 | 8/2020 | |

OTHER PUBLICATIONS

Website Retrieved from: <https://www.cancer.org/cancer/managing-cancer/treatment-types/immunotherapy/immune-checkpoint-inhibitors.html#:~:text=CTLA%2D4%20inhibitors,-CTLA%2D4%20is&text=Ipilimumab%20(Yervoy)%20and%20tremelimumab%20(,1%20or%20PD%2DL1%20inhibitor>. Retrieved on Oct. 18, 2024. (Year: 2024).*
Kumar and Ballas, NEJM, 378(12): Mar. 22, 2018.*
Postow et al., NEJM, 37(2): 158-168, Jan. 11, 2018.*
Chhabra et al. Biology of Blood and Marrow Transplantation, 25: 73-85, ePub Aug. 25, 2018.*
International Search Report and Written Opinion issued on Jun. 10, 2020 for corresponding PCT Application No. PCT/EP2020/052554.
Semper, H. et al., "Drug-induced myocarditis after nivolumab treatment in a patient with PDL1-negative squamous cell carcinoma of the lung", Lung Cancer, vol. 99, 2016, pp. 117-119 XP002791618.
Frigeri, Mauro et al., "Immune Checkpoint Inhibitor-Associated Myocarditis: A New Challenge for Cardiologists", Canadian Cardiovascular Society, vol. 34, 2018, pp. 92.e1-92.e3 XP002791619.
Sanchez De Cos Escuin, Julio, "New Immunotherapy and Lung Cancer", Archivos De Bronconeumologia, vol. 53, No. 12, 2017, pp. 682-687 XP085289232.
Scalapino, Kenneth J. et al., "CTLA-4: a key regulatory point in the control of autoimmune disease", Immunological Reviews, vol. 223, 2008, pp. 143-155 XP002791620.
Antoni Ribas et al., "Antitumor activity in melanoma and anti-self responses in a phase I trial with the anti-cytotoxic T lymphocyte-associated antigen 4 monoclonal antibody CP-675,206", Journal of Clinical Oncology, vol. 23, No. 35, 2005, pp. 8968-8977 XP002702513.
Peter Attia et al., "Autoimmunity Correlates With Tumor Regression in Patients With Metastatic Melanoma Treated With Anti-Cytotoxic T-Lymphocyte Antigen-4", Journal of Clinical Oncology, vol. 23, No. 25, 2005, pp. 6043-6053 XP055184252.
Ravneet Bajwa et al., "Adverse Effects of Immune Checkpoints Inhibitors (Programmed Death-1 Inhibitors and Cytotoxic T-Lymphocyte-Associated Protein-4 Inhibitors): Results of a Retrospective Study," Journal of Clinical Med. Research., vol. 11, No. 4, 2019, pp. 225-236.

(Continued)

*Primary Examiner* — Kimberly Ballard
*Assistant Examiner* — Stacey N Macfarlane
(74) *Attorney, Agent, or Firm* — POLSINELLI PC

(57) ABSTRACT

The invention relates to the use of CTLA4 agonist for treating or preventing adverse events in patient treated with an immune checkpoint inhibitor.

21 Claims, No Drawings

(56) References Cited

OTHER PUBLICATIONS

Sabrina Ceeraz et al., "Immune checkpoint receptors in regulating immune reactivity in rheumatic disease," Arthritis Research & Therapy, vol. 16, No. 469, 2014, pp. 1-12.

Sarju Ganatra et al., "Immune Checkpoint Inhibitor-Associated Myocarditis," The Oncologist, vol. 23, 2018, pp. 879-886.

Jiun-Ruey Hu et al., "Cardiovascular toxicities associated with immune checkpoint inhibitors," European Society of Cardiology, Cardiovascular Research, vol. 115, 2019, pp. 854-868.

Changhua Ji et al., "Myocarditis in Cynomolgus Monkeys Following Treatment with Immune Checkpoint Inhibitors," Clinical Cancer Research, Translational Cancer Mechanism and Therapy, 2019, pp. 4735-4748.

Douglas B. Johnson et al., "Fulminant Myocarditis with Combination Immune Checkpoint Blockade," HHS Public Access, vol. 375, No. 18, 2016, pp. 1749-1755.

Robb D. Kociol et al., "Recognition and Initial Management of Fulminant Myocarditis," AHA Scientific Statement, vol. 141, 2020, pp. e1-e24.

Kenar D. Jhaveri et al., "Adverse Events Associated with Immune Checkpoint Blockade," The New England Journal of Medicine, vol. 378, No. 12, 2018, pp. 1163-1165.

Javid J. Moslehi et al., "Increased reporting of fatal immune checkpoint inhibitor-associated myocarditis," Correspondence, vol. 391, 2018, p. 933.

Salem, J-E. et al., "Supplementary Appendix," The Lancet—Oncology, 2018, pp. 1-6.

Salem, J-E. et al., "Cardiovascular toxicities associated with immune checkpoint inhibitors: an observational, retrospective, pharmacovigilance study," Articles, vol. 19, 2018, pp. 1579-1589.

Kazuko Tajiri et al., "Immune checkpoint inhibitor-related myocarditis," Japanese Journal of Clinical Oncology, vol. 48, No. 1, 2018, pp. 7-12.

Michiel Van Der Vlist et al., "Immune checkpoints and rheumatic diseases: what can cancer immunotherapy teach us?" Nature Reviews, 2016, pp. 1-12.

Giacomo Veronese et al., "Fulminant myocarditis: Characteristics, treatment, and outcomes," Review, Anatol J. Cardiol., vol. 19, 2018, pp. 279-286.

Daniel Y. Wang et al., "Fatal Toxic Effects Associated With Immune Checkpoint Inhibitors," Research: Original Investigation, 2018, pp. E1-E8.

Spencer C. Wei et al., "A Genetic Mouse Model Recapitulates Immune Checkpoint Inhibitor-Associated Myocarditis and Supports a Mechanism-Based Therapeutic Intervention," Research Brief, Cancer Discovery, 2021, pp. 614-626.

Yu-Wen Zhou et al., "Immune Checkpoint Inhibitor-Associated Cardiotoxicity: Current Understanding on Its Mechanism, Diagnosis and Management," Frontiers in Pharmacology, vol. 10, Article 1350, 2019, pp. 1-20.

Bharat Kumar et al., "Adverse Events Associated with Immune Checkpoint Blockade," The New England Journal of Medicine, vol. 378, No. 12, 2018, p. 1164.

Mathieu Kerneis et al., "Abatacept for Severe Immune Checkpoint Inhibitor-Associated Myocarditis," The New England Journal of Medicine, vol. 380, No. 24, 2019, pp. 2377-2379.

Michael A. Postow et al., "Immune-Related Adverse Events Associated with Immune Checkpoint Blockade," The New England Journal of Medicine, vol. 378, No. 2, 2018, pp. 158-168.

Jiun-Ruey Hu et al., "Cardiovascular toxicities associated with immune checkpoint inhibitors," Cardiovascular Research, vol. 115, 2019, pp. 854-868.

Jiun-Ruey Hu et al., "Cardiovascular toxicities associated with immune checkpoint inhibitors," Cardiovascular Research, vol. 1323, 2018, pp. 1-52.

Osnat I. B. Zadok, et al., "Immune-Checkpoint Inhibitor-Induced Fulminant Myocarditis and Cardiogenic Shock," JACC: Cardiooncology, vol. 1, No. 1, 2019, pp. 141-144.

Lars Michel et al., "Cardiotoxicity from immune checkpoint inhibitors," IJC Heart & Vasculature, vol. 25, 2019, pp. 1-7.

Francis J. Dumont, "Technology evaluation: Abatacept, Bristol-Myeres Squibb," Current Opinion in Molecular Therapeutics, vol. 6, No. 3, 2004, pp. 318-330.

NICE National Institute for Health and Care Excellence, "Immunosuppressive therapy for kidney transplant in adults," 2023, pp. 1-43.

NICE National Institute for Health and Care Excellence, "Adalimumab, etanercept, infliximab, rituximab and abatacept for the treatment of rheumatoid arthritis after the failure of a TNF inhibitor," 2022, pp. 1-72.

Mark C. Genovese et al., "Abatacept for Rheumatoid Arthritis Refractory to Tumor Necrosis Factor a Inhibition," The New England Journal of Medicine, vol. 353, No. 11, 2005, pp. 1114-1123.

Nobunori Takahashi et al., "Longterm Efficacy and Safety of Abatacept in Patients with Rheumatoid Arthritis Treated in Routine Clinical Practice: Effect of Concomitant Methotrexate after 24 Weeks," The Journal of Rheumatology, vol. 42, No. 5, 2015, pp. 786-793.

Anna Tjärnlund et al., "Abatacept in the treatment of adult dermatomyositis and polymyositis: a randomised, phase IIb treatment delayed-start trial," Clinical and epidemiological research, vol. 77, 2018, pp. 55-62.

Anne M. Kerola et al., "Abatacept as a successful therapy for myositis—a case-based review," Clinical Rheumatology, vol. 34, 2015, pp. 609-612.

Bita Arabshahi et al., "Abatacept and Sodium Thiosulfate for Treatment of Recalcitrant Juvenile Dermatomyositis Complicated by Ulceration and Calcinosis," Journal of Pediatrics, vol. 160, No. 3, 2012, pp. 520-522.

History of Changes for Study: NCT02594735, "Abatacept in Juvenile Dermatomyositis (AID)," 2022, pp. 1-6.

History of Changes for Study: NCT03215927, "Abatacept for the Treatment of Myositis-associated Interstitial Lung Disease (ATtackMy-ILD)," 2023, pp. 1-6.

Bo Han et al., "CTLA4-Ig Relieves Inflammation in Murine Models of Coxsackievirus B3-Induced Myocarditis," Canadian Journal of Cardiology, vol. 28, 2012, pp. 239-244.

Satoru Abe et al., "Prevention of Experimental Autoimmune Myocarditis by Hydrodynamics-Based Naked Plasmid DNA Encoding CTLA4-Ig Gene Delivery," Journal of Cardiac Failure, vol. 11, No. 7, 2005, pp. 557-564.

Liu Wei et al., "Upregulation of CD4+CD25+ T lymphocyte by adenovirus-mediated gene transfer of CTLA4lg fusion protein in experimental autoimmune myocarditis," Autoimmunity, vol. 39, No. 4, 2009, pp. 289-298.

History of Changes for Study: NCT03619876, "Effects of Abatacept in Myocarditis in Rheumatoid Arthritis (AMIRA)," 2023, pp. 1-4.

Albert J. Czaja et al., "Advances in the Diagnosis, Pathogenesis, and Management of Autoimmune Hepatitis," Gastroenterology, vol. 139, 2010, pp. 58-72.

The Access Trail Group, "Treatment of Lupus Nephritis With Abatacept," Arthritis & Rheumatology, vol. 66, No. 11, 2014, pp. 3096-3104.

Evelyne Israel-Assayag et al., "Blockade of T Cell Costimulation by CTLA4-Ig Inhibits Lung Inflammation in Murine Hypersensitivity Pneumonitis," The Journal of Immunology, vol. 163, 1999, pp. 6794-6799.

Carol A. Langford et al., "A Randomized, Double-Blind Trial of Abatacept (CTLA4-IG) for the Treatment of Giant Cell Arteritis," Arthritis Rheumatology, vol. 69, No. 4, 2017, pp. 837-845.

Kathleen Y. Wang et al., "An Adult with Enteritis and Hypogammaglobulinemia Found to Have Heterozygous STXBP2 Mutation," Journal of Allergy and Clinical Immunology, 2017, p. 1.

Gulbu Uzel et al., "Management of Cytopenias in CTLA4 Haploinsufficiency Using Abatacept and Sirolimus," Blood, vol. 132, 2018, pp. 1-3.

Letters to the Editor, "Abatacept alleviates severe auto-immune symptoms in a patient carrying a de novo variant in CTLA-4," Journal of Allergy and Clinical Immunology, vol. 137, No. 1, 2016, pp. 327-330.

(56)    References Cited

OTHER PUBLICATIONS

Joe-Elie Salem et al., "Spectrum of cardiovascular toxicities of immune checkpoint inhibitors: A pharmacovigilance study," Lancete Oncol., vol. 19, No. 12, 2018, pp. 1579-1589.

William J. Sandborn et al., "Abatacept for Crohn's Disease and Ulcerative Colitis," Gastroenterology, vol. 143, 2012, pp. 62-69.

Lucy Boyce Kennedy et al., "A Review of Cancer Immunotherapy Toxicity," CA Cancer J Clin, vol. 70, No. 2, 2020, pp. 86-104.

Lucy Boyce Kennedy et al., "A Review of Cancer Immunotherapy Toxicity," National Library of Medicine, Abstract, 2020, p. 1.

Anonymous, "Orencia (abatacept). An overview of Orencia and why it is authorised in the EU," European Medicines Agency, 2019, pp. 1-4.

Rakiba Belkhir et al., "Rheumatoid arthritis and polymyalgia rheumatica occuring after immune checkpoint inhibitor treatment," Clinical and epidemiological research, vol. 76, 2017, pp. 1747-1750.

History of Changes for Study: NCT01714817, "Efficacy and Safety Study of Abatacept to Treat Lupus Nephritis," 2021, pp. 1-25.

History of Changes for Study: NCT01714817, "Efficacy and Safety Study of Abatacept to Treat Lupus Nephritis," 2021, pp. 1-50.

Article: "ORENCIA 250 mg powder for concentrate for solution for infusion," 2024, pp. 1-20 https://www.medicines.org.uk/emc/product/334/smpc/print.

J.M. Michot et al.; "Immune-related adverse events with immune checkpoint blockade: a comprehensive review," European Journal of Cancer, vol. 54, 2016, pp. 139-148 http://dx.doi.org/10.1016/j.ejca.2015.11.016.

Article: "Induce—Definition and Meaning from Merriam-Webster Dictionary" https://www.merriam-webster.com/dictionary/induce.

Michael Conroy et al.; "Immune-related adverse events and the balancing act of immunotherapy," Nature Communications, vol. 13, No. 392, 2022, pp. 1-4.

Article:"Rituximab," Wikipedia, The Free Encyclopedia, pp. 1-13.

Erik A. Ranheim et al.; "Elevated Expression of CD80 (B7/BB1) and Other Accessory Molecules on Synovial Fluid Mononuclear Cell Subsets in Rheumatoid Arthritis," Arthritis & Rheumatism vol. 37, No. 11, Nov. 1994, pp. 1637-1646.

Dhiren Kumar et al.; "Belatacept As an Alternative to Calcineurin inhibitors in Patients with Solid Organ Transplants," Frontiers in Medicine, vol. 4, Article 60, 2017, pp. 1-9.

Joe-Elie Salem et al.; "Abatacept/Ruxolitinib and Screening for Concomitant Respiratory Muscle Failure to Mitigate Fatality of Immune-Checkpoint Inhibitor Myocarditis," Cancer Discovery, 2023, pp. 1100-1115.

Anroop B. Nair et al.; "A simple practice guide for dose conversion between animals and human," J. Basic Clin Pharma., vol. 7, 2016, pp. 27-31.

Article: "Study Details | Trial of Orencia in Patients With Myasthenia Gravis," National Library of Medicine, 2019 https://clinicaltrials.gov/study/NCT03059888.

* cited by examiner

METHOD FOR TREATING CHECKPOINT INHIBITORS INDUCED ADVERSE EVENTS

CROSS-REFERENCE TO RELATED APPLICATIONS

This application is a national stage application (under 35 U.S.C. § 371) of PCT/EP2020/052554, filed Feb. 3, 2020, which claims benefit of European Application No. 19305128.1, filed Feb. 4, 2019, which are incorporated herein by reference in their entireties.

The invention relates to the treatment of checkpoint inhibitors induced adverse events.

Checkpoint inhibitor therapy is a form of cancer immunotherapy that has revolutioned oncology treatment. It consists in targeting immune checkpoints, which are key regulators of the immune system that stimulate or inhibit its actions. Checkpoint therapy in oncology aims at blocking inhibitory checkpoints, which tumors use to protect themselves from attacks by the immune system, hence restoring immune system function and fighting the tumor.

The currently approved immune checkpoint inhibitors (ICI) target the molecules CTLA4 (Cytotoxic T-Lymphocyte associated protein 4), PD-1 (the transmembrane programmed cell death 1 protein, also called PDCD1 and CD279), and PD-L1, which is the PD-1 ligand (or CD274). PD-1 acts as a key regulatory role on T cell activities, and cancer-mediated upregulation of PD-L1 on the cancer cell surface may inhibit T cells recognition and action against these cells. Antibodies against PD-1 or PD-L1 block the interaction between these proteins and allow T-cells to attack the tumor.

Another inhibitory checkpoint targeted in oncology is CTLA-4 (CD152), a protein receptor constitutively expressed in regulatory T cells and upregulated in conventional T cells after activation. It acts as an inhibitory switch of the immune system when it binds to CD80 or CD86 expressed on the surface of antigen-presenting cells.

However, the activation of the immune system after use of such immune checkpoint inhibitors may also lead to immune related adverse events (irAE) affecting potentially any organ.

Although rare, fulminant, and fatal irAE on ICI may occur in ~0.36-1.23% of treated patients (Wang et al. JAMA Oncol 2018; 4:1721-8). Severe and fatal toxicities are more common with anti-CTLA4 therapies, particularly when combined with PD1 or PDL1 blockers. ICI induced myocarditis occurs rarely (<1%) but is the irAE with the highest fatality rate. In the largest case-series of 122 myocarditis cases worldwide, the fatality rate was reported to be 50% with an earlier onset and higher fatality rate with ICI combination therapy versus monotherapy (Salem et al. Lancet Oncol 2018; 19:1579-89). Interestingly, ICI myocarditis occurred generally after few ICI doses (n=1-3) and were often associated with concurrent muscular, pulmonary and hepatic irAE, including myositis (25%) with a peculiar phenotype often associated with occulomotor and diaphragmatic dysfunction. A main contributing cause of death in ICI myocarditis is early progressive and refractory cardiac electrical instability (heart blocks and ventricular arrhythmias) and cardiac dysfunction leading to cardiogenic shock, often resistant to intense immunosuppression.

While rigorous studies for the treatment of irAEs have not been performed, consensus guidelines recommend initial treatment with high-dose corticosteroids with progressive tapering and holding ICI (Brahmer et al, J Clin Oncol 2018; 36:1714-68). Corticosteroids doses range from bolus of 0.5-2 mg/kg/day of prednisone up to 1 g/day methylprednisolone, depending on severity of clinical presentation. If symptoms and laboratory findings do not improve or worsen with steroids, other immunosuppressive drugs (mycophenolate-mofetil, cyclophosphamide, cyclosporine, tacrolimus, mTors inhibitors, methotrexate, azathioprine, antithymocyte globulin, alemtuzumab, JAK inhibitors, TYK2 inhibitors, infliximab, and rituximab) can be considered, depending on organs affected. In case of associated myositis and/or myasthenia gravis, intravenous immunoglobulin or plasmapheresis can be considered when presentations are severe and/or corticosteroid-resistant. In a subset of patients with fulminant, and chronic toxicities, however, available immunosuppresants produce suboptimal results (i.e. the 1.23% of patients who die from PD1/CTLA4 blockade induced toxicities).

Thus, improved reversal or "antidote" strategies are needed.

The invention thus relates to a CTLA4 agonist for use thereof in the treatment or prevention of an adverse event induced by treatment with an immune checkpoint inhibitor.

In particular, such use is particularly adapted when the adverse event is a de novo event, i.e. is not related to a preexisting immune condition. In this embodiment, it is preferred when the patient has not been diagnosed with an auto-immune disease prior to the inset of the treatment with the immune checkpoint inhibitor.

The proposed use is also of particular interest when the adverse event is T-cell and/or macrophage driven, i.e. involving infiltration of CD4+ and/or CD8+ T cells and/or CD68+ macrophages, with minimal or no implication of antibodies (no presence of antibody deposits).

By CTLA4 agonist, it is intended to designate a molecule that provides the same effect as of CTLA4. In particular, a CTLAA4 agonist is a substance that binds to the same cellular receptors as the CTLA4 reference substance (in particular that binds to CD80 or CD86), and produces, at least in part, the same effects (in particular that would switch off the immune system response).

One can cite, as CTLA4 agonists, soluble version of the extracellular domain of CTLA-4, either by themselves, or preferably fused with another peptide or protein. In particular, said other peptide or protein may be the Fc region (or Fc fragment) of an IgG protein. Presence of this other peptide or protein would stabilize the polypeptide comprising the extracellular domain of CTLA-4. When this other protein or peptide is the Fc fragment of the IgG protein, this would assist the binding to the antigen-presenting cells. preferably the IgG protein is a IgG1 protein. However, it is possible to use a Fc fragment from another IgG protein (i.e IgG2, IgG4, . . . ).

Two CTLA4 agonists are currently on the market for other indications. Abatacept and belatacept are fusion proteins composed of the Fc region of the immunoglobulin IgG1 fused to the extracellular domain of CTLA-4. They differ from each other by two amino acids.

The mode of action of these two polypeptides is to bind to the CD80 and CD86 molecules present at the surface of the antigen presenting cell in order to prevent such to provide the second (costimulatory) signal necessary to activate T cells (the first signal being the one provided by the recognition of the major histocompatibility complex (MHC), combined with the antigen.

In a specific embodiment, the CTLA4 agonist is abatacept.

In another embodiment, the CTLA4 agonist is belatacept

The CTLA4 agonist can therefore be used in a method for treating, or in a method for preventing, occurrence of an adverse event induced by a treatment with an immune checkpoint inhibitor, comprising the step of administering an effective amount of the CTLA4 agonist to a patient in need thereof. An effective amount, or therapeutic amount, is the amount sufficient to obtain beneficial or desired results, such as clinical results (remission of the symptoms of the immune related adverse events). The "effective amount" may depend upon the type of immune related adverse event, and upon the context in which it is being applied. In the context of the invention, an effective amount of a CTLA4 agonist is, for example, an amount sufficient to achieve a reduction in the severity of the immune related adverse event, as compared to the response obtained without administration of the agonist.

As the immune related adverse event induced by the treatment with checkpoint inhibitors, one can cite colitis, pneumonitis, hepatitis, hypophysitis, neurologic adverse effects (including encephalitis, myasthenia gravis, Guillain-Barre syndrome), adrenal adverse effect, myositis, myocarditis, hematologic adverse effects (including hemolytic anemia, immune thrombocytopenic purpura, and aplastic anemia), nephritis, pancreatitis, and type 1 diabetes. All these diseases are immune-mediated, and linked to the administration of ICI, that exacerbate the immune system of the patient.

The CTLA4 agonist is particularly interesting for treating an immune-mediated myocarditis, in particular fulminant myocarditis. As indicated above, being able to treat this adverse effect is of particular interest as it is the most fatal one observed after use of ICI.

Fulminant myocarditis (FM) is a peculiar clinical condition and is an acute form of myocarditis, whose main characteristic is a rapidly progressive clinical course with the need for hemodynamic support (Kociol et al, Circulation. 2020 Jan. 6:CIR0000000000000745).

Johnson et al (N Engl J Med. 2016 Nov. 3; 375(18):1749-1755) showed that selective clonal T-cell populations, identical to those present in tumors and skeletal muscle, infiltrated the myocardium, concluding that this event is a T-cell-driven drug reaction. These authors also showed that this kind of fuminant myocarditis, when present in humans, doesn't mainly involve antibodies as immunofluorescence studies showed no antibody deposits. T-cell and/or macrophage driven pathogenesis was also reported by Ganatra and Neilan (Oncologist. 2018 August; 23(8):879-886), Ji et al (Clin Cancer Res. 2019 Aug. 1; 25(15):4735-4748) and Champion S N et al (Mod Pathol. 2020 January; 33(1):99-108). This clinical results, observed in patients, are thus in contrast to the data reported in the model of Wand et al (Int Immunol. 2010 June; 22(6):443-52) which evidenced production of high-titer auto-antibodies against cardiac myosin.

The immune checkpoint inhibitor used for the patient's treatment before occurrence of the adverse effect is any such drug in this class.

In particular, one can cite:

PD-1 inhibitors: IgG4 PD1 antibody nivolumab, pembrolizumab, partalizumab (PDR001) developed by Novartis, pidilizumab developed by Cure Tech, AMP-224 or AMP-514 both developed by GlaxoSmithKline, cemiplimab developed by Regeneron and Sanofi, toripalimab developed by Shanghai Junshi, spartalizumab, developed by Novartis, cetrelimab (JNJ-63723283) developed by Janssen, or sasanlimab (PF-06801591) developed by Pfizer.

PD-L1 inhibitors: atezolizumab developed by Roche Genentech, avelumab developed by Merck Serono and Pfizer or durvalumab developed by AstraZeneca.

Anti-CTLA4: ipilimumab or tremelimumab.

The CTLA4 agonist is used at the dosage similar to (about 10 mg/kg for abatacapet and belatacept, and up to about 20 mg/kg, kowing that belatacept is 2 to 3 times more potent than abatacept) or up to 4 times higher than those dosages preconized by the manufacturer and according to good practice in the art. Choice of the appropriate dosase may be adapted by the physician depending on the severity of the clinical presentation and evolution on treatment. In fact, said CTLA4 agonist may be generally administered at a dose of 5 mg/kg up to 40 mg/kg per dose.

As a matter of illustration, abatacept can be used as an intravenous composition, with a 30 minutes perfusion at a dosasge as indicated below, corresponding to about 10 mg/kg per administration. After the first injection, abatacept is to be administered again at weeks 2, 4 and then every 4 weeks (or until the clinical state of the patient with regards to the induced adverse effect has ameliorated, which is generally obtained within 3-4 weeks. Alternatively, in the most severe presentation, abatacept can be used at 20 mg/kg or even 30 mg/kg per dose every week up up to 6 weeks and then every two weeks until reversion of the immune related adverse event. Consequently, three injections (weeks 0, 2 and 4) and up to 20 injections (week 1, 2, 3, 4, 5, 6, 8, 10, 12, 14, 16, 18, 20, . . . 36), can be needed in the present application. The standard dose is of 500 mg (powder) for patient weighting less than 60 kg, 750 mg for patients weighting between 60 and 100 kg and 1000 mg for patients weighting more than 100 kg. This dose can be doubled or tripled depending on clinical presentation (severity of the immune related adverse event).

When belatacept is used, one can use a dosase of 10 mg/kg (or even 20 mg/kg) at day 1, then 10 mg/kg (or even 20 mg/kg) at days 4, 14 and 28. The dosage may then be lowered, depending on the clinical improvement of the patient, or increased in terme of frequency (days 1, 4, 14, 21, 28 and up to one per week until clinical improvement).

As indicated above, the dose administered to the patient is chosen so as to be therapeutically effective. It is thus possible to use higher amount of such products for the first injections in order to try to quickly stop the immune system reaction, and then lower the dose when the markers of the immune-induced disease become normal again.

In combination with administration of CTLA-4 agonists, as described above, glucocorticoids at high dose (up to 1 g/day methylprednisone equivalent for few days) and or other immunossupressants may be also be used. These latter immunosuppresants are preferentially antimetabolites (such as mycofenolate mofetil, azathiatrine, methotrexate), anti-calcineurin (also designated as calcineurin inhibitors) (ciclosporin, tacrolimus), MTOR inhibitors (sirolimus, temsirolimus, everolimus), anti-thymoglubin, intravenous immunoglobulin, interleukin-6 inhibitors (tocilizumab, siltuximab), interleukin-1 pathway inhibitors (anakinra, rilonacept, canakinumab), TNF-$\alpha$ inhibitors, JAK inhibitors, TYK2 inhibitors or anti CD28. Other compounds that can be used also include basiliximab (chimeric mouse-human monoclonal antibody) or daclizumab (both binding to the a chain (CD25) of the IL-2 receptor of T cells), tocilizumab, also known as atlizumab, humanized monoclonal antibody against the interleukin-6 receptor (IL-6R), and alemtuzumab (monoclonal antibody that binds to CD52).

It is also possible to use plasmapheresis to clear immune check-point inhibitor drug levels in the circulation. In this case, the scheme of administration of the CTLA-4 agonist (in particular abatacept) need to be adapted (readministration), as circulating levels of previsouly administrated agonist have been cleared.

The invention also relates to the CTLA4 agonist for use as indicated above, it is administered with another immunosuppressant, or any other drug as disclosed below, including glucocorticoids, antimetabolites (such as mycofenolate mofetil, azathiatrine, methotrexate), calcineurin inhibitors (ciclosporin, tacrolimus), mtor inhibitors (sirolimus, temsirolimus, everolimus), anti-thymoglubin, intravenous immunoglobulin, interleukin-6 inhibitors (tocilizumab, siltuximab), anti CD52 (alemtuzumab) anti CD25 (basiliximab, daclizumab), interleukin-1 pathway inhibitors (anakinra, rilonacept, canakinumab), TNF-α inhibitors, JAK inhibitors, TYK2 inhibitors and anti CD28. Said co-administration can be simultaneous, separate or sequential (spread out over time)

The invention also relates to a composition containing a CTLA4 agonist and an immunosuppressant or any other drug as disclosed above, for simultaneous, separate or sequential (spread out over time) use thereof in the treatment or prevention of an adverse event induced by a treatment with an immune checkpoint inhibitor.

The invention also relates to a method for treating or preventing an adverse event induced by a treatment with an immune checkpoint inhibitor, comprising administering a therapeutically active amount of a CTLA4 agonist to a subject in need thereof, with a simultaneous, separate or sequential (spread out over time) administration of an effective amount of an immunosuppressant to the subject.

The invention also relates to a CTLA4 agonist for use thereof in the treatment of an adverse event induced by a treatment with an immune checkpoint inhibitor, in a patient in need thereof, wherein said patient has been subject to a plasmapheresis prior to administration of the CTLA4 agonist. As indicated above, such plasmapheresis makes it possible to clear immune check-point inhibitors levels in the circulation of the patient.

The invention also relates to a method for treating a subject in need thereof, wherein said subject present an adverse effect induced by a treatment with an immune checkpoint inhibitor, comprising performing a plasmapheresis to the subject (so as to clear immune check-point inhibitors levels in the circulation of the subject) and administering an effective amount of a CTLA4 agonist (alone or with another immunosuppressant) prior and after plasmapheresis.

It is generally envisaged to make only a limited amount of administrations to the patient (up to 20), and to stop the treatment when the patient general condition has improved, when the specific immune-derived disease has disappeared, or when it is considered as non dangerous anymore by the physicians. In a specific embodiment, the treatment should last for a few weeks or maximum months (up to 7 times the half-life of the liable immune-checkpout inhibitor administered), with an administration every week or two weeks, from five to eight and up to 40 weeks. In this case, there would be multiple administration of the CTLA4 agonist provided to the patient.

The CTLA4 agonist can be in a form suitable for oral administration. However, in view of the fact that known CTLA4 agonist are in the form of polypeptides, such agonists would have to be protected from gastric degradation.

It is thus preferred when the CTLA4 agonist is a form suitable for injectable administration. Preferably, such administration is a intravenous injection, intra-muscular or subcutaneous injection.

In specific embodiment, the CTLA4 agonist is in the form of a slow release composition, which would allow to decrease the number of injections.

EXAMPLES

The following examples demonstrates the utility and workability of CTLA4 agonists (such as CTLA4-Immunoglobulin fusion proteins: abatacept and belatacept) as a potential antidote for life-threatening irAE resistant to standard management, such as myocarditis.

Abatacept was used in a 66 yo woman presenting with life-threatening immune checkpoint inhibitor induced myocarditis associated with myositis, oculomotor weakness, arthritis flare-up and hepatitis. These irAE occurred after three doses of nivolumab (Anti-PD-1) given for lung adenocarcinoma invading the pleura. She was former smoker and had a history of sinus tachycardia on betablockers, systemic lupus on hydroxychloroquine and a thymoma treated by radiotherapy and surgery 23 years ago complicated by a phrenic nerve ligation (with secondary pulmonary restrictive syndrome).

The patient initially presented with ptosis, diplopia and a painful paresis affecting proximal muscles ~1.5 months after starting nivolumab. Chest pain, electrocardiogram abnormalities (precordial diffuse ST-elevation, bundle branch block), were identified one week later. Troponin-T (1616 ng/L) and NT-proBNP (4172 ng/L) were increased at intensive care unit admission. Coronary angiogram revealed normal arteries; echocardiogram showed a subnormal left ventricular ejection fraction (50%) with a mild apical hypokinesis and a concentric remodeling. Cardiac magnetic resonance imagery (MRI) confirmed myocarditis (positive septo-apical late gadolinium enhancement).

She initially received a bolus of intravenous methylprednisolone (500 mg/day for 3 days). Troponin-T (6158 ng/L) and NT-proBNP (6838 ng/L) increased, with no amelioration of her clinical symptoms.

Five sessions of plasmapheresis were performed, and a rapid decrease of nivolumab plasma concentration to almost undetectable levels was observed, but with no effect on troponin (plateau ~5000-6000 ng/L). Of note, etiologic work-up was negative for myositis specific or anti-acetylcholine receptor antibodies; electromyography showed a myogenic syndrome without sign of neuromeuromuscular dysfunction and muscular biopsy revealed an important T-cell and macrophage infiltration with multiple lesions of focal necrosis. Despite high dose steroids and plasmapheresis, the patient developed ventricular hyper-excitability (10-14,000 ventricular extra-systoles per day vs. none at admission). Abatacept (intravenous, 500 mg every 2 weeks; 5 doses total) treatment was then initiated. Troponin began to decrease the day after the first abatacept dose, and progressively over months to a minimum of 504 ng/L while prednisone was progressively tapered. Ventricular hyperexcitability progressively and completely disappeared after 4 doses of abatacept (24 h-holter normalized). Ejection fraction remained normal throughout follow-up, with NT-proBNP decreasing and stabilizing at slightly elevated levels (1000-1500 ng/L). Myocarditis (arrhythmias), and myositis (muscular weakness, ptosis, facial paralysis) symptoms progressively regressed from maximum grade 4 to grade 1. Hepatitis (maximum grade 3) and arthritis flare-up also resolved on abatacept. Patient was discharged 7.5 weeks after initial admission. Importantly, a cross-sectional imaging performed one month after abatacept start showed no progression (30 mm maximal diameter before immunotherapy, 36 mm after 3 doses of nivolumab, 36 mm after 2 doses of abatacept).

In an other case, a 84 yo male with lung cancer developed an immune-checkpoint inhibitor induced myocarditis, associated with myositis with diaphragmatic involvement after 2 doses of pembrolizumab (35 days after first dose). Abatacept was also used effectively to reverse these immune-related adverse event. Abatacept was used at the dose of approximatively 20 mg/kg (1500 mg/dose) every week for 6 weeks combined with mycophenolate mofetil (1 g*2/day) and glucocortidoids (1 g methylprednisolone for 3 days, then 2 mg/kg for two weeks followed by 1 mg/kg for two weeks and progressive tapering of 5 mg every two weeks). Of note, 2 plasmapheresis sessions were also performed after the fourth abatacept dosing. Abatacept is also to be continued for at least 4 doses every two weeks.

Discussion

Current treatment recommendations of irAE are based on anecdotal evidence, and the results reported above work raise the question about the place that CTLA4 agonists should have in the treatment of life-threatening irAE. It remains unclear whether the presence of severe irAEs correlates with improved survival in patients treated with ICI; and to what extent treating irAE with immunosuppression may impair and diminish anti-tumor effects of ICI. For this patient, it was considered that her severe myocarditis presentation complicated by ventricular hyper-excitability resistant to corticosteroids and plasmapheresis threatened her life, potentially within days. Therefore, treatment with abatacept was initiated, despite potential pro-tumorigenic effects. The risk-benefit balance of this strategy needs to be evaluated for each patient.

Broad spectrum immunosuppressive drugs (i.e, corticosteroids or cyclophosphamide) affect multiple immune cells and other unwanted organs leading to a myriad of adverse drug reactions. In the present case, CTLA4 agonists inhibit CD28-B7 mediated T-cell co-stimulation at the level of dendritic cells, and thus abrogate activation of the T-cells upstream of the CTLA4 and PD1/PDL1 pathways in the T-cells. Thus, these should lead to rapid global T-cell anergy with limited off-target effects, and specifically reversing the pathways activated by ICI. This presents an advantage with regards to other proposed immunosuppressants which have variable mechanisms of action, generally very remotely interacting with CTLA4 and PD1/PDL1 molecular cascades.

In the above example, are presented cases of recovered severe ICI induced myotoxicities including myocarditis, myositis with diaphragmatic involvement, and hepatatis treated with abatacept, which further support the potential use of CTLA4 agonists as antidotes for ICI induced life-threatening irAE.

The invention claimed is:

1. A method for treating an adverse event induced by a treatment with an immune checkpoint inhibitor comprising administering an effective amount of abatacept to a patient in need thereof, wherein the adverse event is a de novo adverse event induced by the treatment with the immune checkpoint inhibitor, and not related to a preexisting immune condition in the patient treated with the immune checkpoint inhibitor.

2. The method of claim 1, wherein the adverse event is an immune-mediated disease selected from the group consisting of myotoxicity, colitis, pneumonitis, hepatitis, hypophysitis, neurologic adverse effect, adrenal adverse effect, myositis, hematologic adverse effect, pancreatitis, endocrinological adverse effect, and nephritis.

3. The method of claim 1, wherein the checkpoint inhibitor is selected from the group consisting of PD-1 inhibitors, PD-L1 inhibitors, anti-CTLA4, and combinations thereof.

4. The method of claim 3, wherein the checkpoint inhibitor is a PD-1 inhibitor selected from the group consisting of nivolumab, pembrolizumab, pidilizumab, AMP-224, AMP-514, cemiplimab, toripalimab, spartalizumab, cetrelimab, and sasanlimab.

5. The method of claim 3, wherein the checkpoint inhibitor is a PD-L1 inhibitor selected from the group consisting of atezolizumab, avelumab, and durvalumab.

6. The method of claim 3, wherein the checkpoint inhibitor is an anti-CTLA4 selected from the group consisting of ipilimumab and tremelimumab.

7. The method of claim 1, further comprising administering to the patient an immunosuppressant, wherein abatacept the CTLA4 and the immunosuppressant are administered simultaneously, separately, or sequentially.

8. The method of claim 7, wherein the immunosuppressant is selected from the group consisting of mycophenolate mofetil, azathioprine, methotrexate, calcineurin inhibitors, cyclosporin, tacrolimus, MTOR inhibitors, sirolimus, temsirolimus, everolimus, anti-thymoglobulin, intravenous immunoglobulin, interleukin-6 inhibitors, tocilizumab, siltuximab, interleukin-1 pathway inhibitors, anakinra, rilonacept, canakinumab, TNF-α inhibitors, JAK inhibitors, TYK2 inhibitors, basiliximab, daclizumab, tocilizumab and alemtuzumab.

9. A method for treating myocarditis induced by treatment with an immune checkpoint inhibitor, the method comprising administering an effective amount of abatacept to a patient in need thereof, wherein the adverse event is a de novo adverse event induced by the treatment with the immune checkpoint inhibitor, not related to a preexisting immune condition in the patient treated with the immune checkpoint inhibitor.

10. The method of claim 9, wherein the checkpoint inhibitor is a PD-1 inhibitor selected from the group consisting of nivolumab, pembrolizumab, pidilizumab, AMP-224, AMP-514, cemiplimab, toripalimab, spartalizumab, cetrelimab, and sasanlimab.

11. The method of claim 9, wherein the checkpoint inhibitor is a PD-L1 inhibitor selected from the group consisting of atezolizumab, avelumab, and durvalumab.

12. The method of claim 9, further comprising administering to the patient an immunosuppressant, wherein the CTLA4 and the immunosuppressant are administered simultaneously, separately, or sequentially.

13. The method of claim 12, wherein the immunosuppressant is selected from the group consisting of mycophenolate mofetil, azathioprine, methotrexate, calcineurin inhibitors, cyclosporin, tacrolimus, MTOR inhibitors, sirolimus, temsirolimus, everolimus, anti-thymoglobulin, intravenous immunoglobulin, interleukin-6 inhibitors, tocilizumab, siltuximab, interleukin-1 pathway inhibitors, anakinra, rilonacept, canakinumab, TNF-α inhibitors, JAK inhibitors, TYK2 inhibitors, basiliximab, daclizumab, tocilizumab and alemtuzumab.

14. A method for preventing an adverse event induced by a treatment with an immune checkpoint inhibitor comprising administering an effective amount of abatacept to a patient in need thereof, wherein the adverse event is a de novo adverse event induced by the treatment with the immune checkpoint inhibitor, not related to a preexisting immune condition in the patient treated with the immune checkpoint inhibitor.

15. The method of claim 14, wherein the adverse event is an immune-mediated disease selected from the group consisting of myotoxicity, colitis, pneumonitis, hepatitis, hypophysitis, neurologic adverse effect, adrenal adverse effect, myositis, hematologic adverse effect, pancreatitis, endocrinological adverse effect, and nephritis.

16. The method of claim 14, wherein the adverse event is myocarditis.

17. The method of claim 14, wherein the checkpoint inhibitor is selected from the group consisting of PD-1 inhibitors, PD-L1 inhibitors, anti-CTLA4, and combinations thereof.

18. The method of claim 17, wherein the checkpoint inhibitor is a PD-1 inhibitor selected from the group consisting of nivolumab, pembrolizumab, pidilizumab, AMP-224, AMP-514, cemiplimab, toripalimab, spartalizumab, cetrelimab, and sasanlimab.

19. The method of claim 17, wherein the checkpoint inhibitor is a PD-L1 inhibitor selected from the group consisting of atezolizumab, avelumab, and durvalumab.

20. The method of claim 17, wherein the checkpoint inhibitor is an anti-CTLA4 selected from the group consisting of ipilimumab and tremelimumab.

21. The method of claim 14, further comprising administering to the patient an immunosuppressant, wherein abatacept and the immunosuppressant are administered simultaneously, separately, or sequentially.

\* \* \* \* \*